United States Patent
Woo et al.

(10) Patent No.: US 11,000,204 B2
(45) Date of Patent: May 11, 2021

(54) DEVICE AND METHOD FOR RECONSTRUCTING LOW-FREQUENCY CONDUCTIVITY IMAGES USING MRI WITHOUT CURRENT INJECTION

(71) Applicant: UNIVERSITY-INDUSTRY COOPERATION GROUP OF KYUNG HEE UNIVERSITY, Yongin-si (KR)

(72) Inventors: Eung Je Woo, Seongnam-si (KR); Oh In Kwon, Seoul (KR); Hyung Joong Kim, Hwaseong-si (KR); Woo Chul Jeong, Incheon (KR); Saurav Zaman Khan Sajib, Yongin-si (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 370 days.

(21) Appl. No.: 16/089,976

(22) PCT Filed: Mar. 29, 2017

(86) PCT No.: PCT/KR2017/003376
§ 371 (c)(1),
(2) Date: Sep. 28, 2018

(87) PCT Pub. No.: WO2017/171379
PCT Pub. Date: Oct. 5, 2017

(65) Prior Publication Data
US 2019/0142296 A1 May 16, 2019

(30) Foreign Application Priority Data
Apr. 1, 2016 (KR) .................. 10-2016-0040043

(51) Int. Cl.
*A61B 5/055* (2006.01)
*G01R 33/563* (2006.01)
(Continued)

(52) U.S. Cl.
CPC ............ *A61B 5/055* (2013.01); *A61B 6/03* (2013.01); *G01R 33/24* (2013.01); *G01R 33/483* (2013.01);
(Continued)

(58) Field of Classification Search
CPC ...................... A61B 5/055; G01R 33/5602; G01R 33/5605; G01R 33/56341; G01R 33/385;
(Continued)

(56) References Cited

U.S. PATENT DOCUMENTS 7,627,155 B2 12/2009 Guo et al.
2010/0013475 A1 1/2010 Kimura
(Continued)

FOREIGN PATENT DOCUMENTS

JP 2007-000625 A 1/2007
JP 2012-157687 A 8/2012
(Continued)

OTHER PUBLICATIONS

Hui Zhang et al., "NODDI: Practical in vivo neurite orientation dispersion and density imaging of the human brain", NeuroImage, 2012, 17 pages, vol. 61.
(Continued)

*Primary Examiner* — Mark D Remaly
(74) *Attorney, Agent, or Firm* — Sughrue Mion, PLLC

(57) ABSTRACT

The present invention relates to a device and method for reconstructing low-frequency conductivity images using MRI without current injection. In the device according to the present invention, low-frequency conductivity is deduced using high-frequency conductivity obtained using MR-EPT,
(Continued)

the calculated directional tensor of ions from the water diffusion tensor in a subject, and the volume fractions and diffusion coefficients of the intracellular/extracellular spaces, and low-frequency conductivity images are reconstructed based on the deduced low-frequency conductivity. According to the present invention, low-frequency conductivity images in a subject to be measured such as the human body and an object may be reconstructed using an MRI device without applying current to the subject.

9 Claims, 5 Drawing Sheets

(51) Int. Cl.
  *G01R 33/24* (2006.01)
  *G01R 33/483* (2006.01)
  *A61B 6/03* (2006.01)
  *G06T 7/00* (2017.01)
  *G01R 33/44* (2006.01)

(52) U.S. Cl.
  CPC ...... *G01R 33/56341* (2013.01); *G06T 7/0002* (2013.01); *G01R 33/443* (2013.01)

(58) Field of Classification Search
  CPC  G01R 33/48; G01R 33/4824; G01R 33/4828; G01R 33/5608; G01R 33/561; G01R 33/5611; G01R 33/5616; G01R 33/5619; G01R 33/56366
  See application file for complete search history.

(56) References Cited

U.S. PATENT DOCUMENTS

| 2015/0253410 | A1* | 9/2015 | Warfield | G01R 33/385 |
| | | | | 324/309 |
| 2016/0061921 | A1* | 3/2016 | Katscher | G01R 33/4828 |
| | | | | 324/309 |

FOREIGN PATENT DOCUMENTS

| JP | 5591493 B2 | 9/2014 |
| KR | 10-2014-0082022 A | 7/2014 |
| KR | 10-2014-0089103 A | 7/2014 |

OTHER PUBLICATIONS

Eung Je Woo et al., "Magnetic resonance electrical impedance tomography (MREIT) for high-resolution conductivity imaging", Physiological Measurement, 2008, 26 pages, vol. 29.

Greg J. Stanisz et al., "An Analytical Model of Restricted Diffusion in Bovine Optic Nerve", Magnetic Resonance in Medicine, 1997, 9 pages, vol. 37.

Jin Keun Seo et al., "Electrical Tissue Property Imaging at Low Frequency Using MREIT", IEEE Transactions on Biomedical Engineering, 2014, 10 pages, vol. 61, No. 5.

International Search Report for PCT/KR2017/003376 dated Jun. 28, 2017.

* cited by examiner

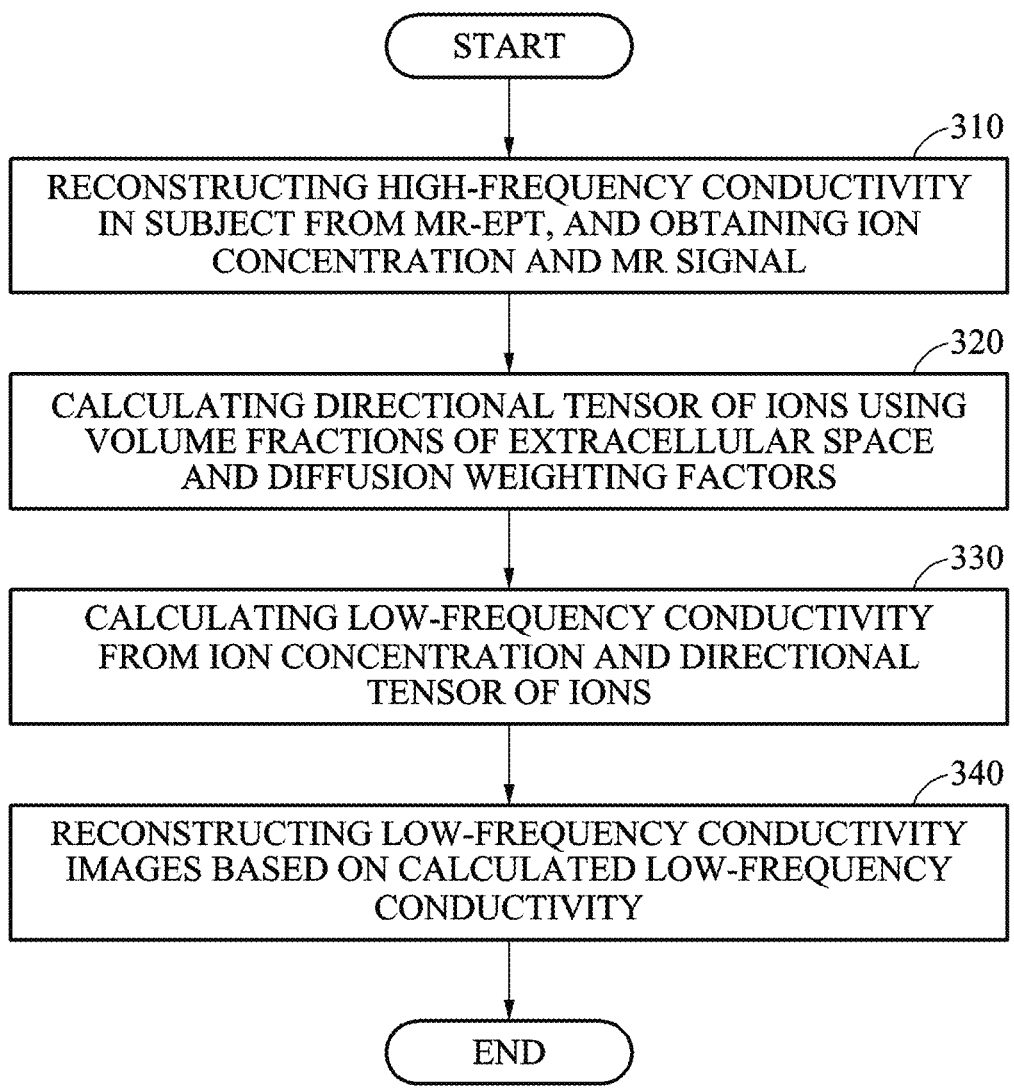

DEVICE AND METHOD FOR RECONSTRUCTING LOW-FREQUENCY CONDUCTIVITY IMAGES USING MRI WITHOUT CURRENT INJECTION

CROSS-REFERENCE TO RELATED APPLICATION

This application is a National Stage of International Application No. PCT/KR2017/003376 filed Mar. 29, 2017, which claims priority to Korean Patent Application No. 10-2016-0040043, filed on Apr. 1, 2016 in the Korean Intellectual Property Office, the disclosure of which is incorporated herein by reference.

TECHNICAL FIELD

The present invention relates to a device and method for reconstructing low-frequency conductivity images using MRI without current injection, wherein a low-frequency conductivity tensor is deduced using high-frequency conductivity obtained using magnetic resonance electric properties tomography (MR-EPT), the calculated directional tensor of ions from the water diffusion tensor in a subject, and the volume fractions and diffusion coefficients of intracellular/extracellular spaces, and based on the deduced low-frequency conductivity tensor, low-frequency conductivity images are reconstructed.

BACKGROUND ART

Water diffusion tensor (D) data measured using a typical magnetic resonance imaging (MRI) device is obtained from Equation 1 below using a diffusion-sensitizing gradient (g):

$$\rho_D = \rho_0 \exp(-bg^T D g), \qquad \text{[Equation 1]}$$

wherein $\rho_0$ denotes a signal obtained without a diffusion-sensitizing gradient, D denotes the water diffusion tensor, b denotes a diffusion weighting factor, g denotes a diffusion-sensitizing gradient, and $g^T$ denotes the transpose vector of a vector g.

In this case, one or more water diffusion tensor values may be obtained by varying the magnitude of the value of the diffusion weighting factor.

In addition, it is known that the conductivity tensor (C) approximately relates to the water diffusion tensor, and the relationship therebetween is shown in Equation 2 below:

$$C = S_D \overline{C} S_D^T, \qquad \text{[Equation 2]}$$

wherein the column vector of the matrix $S_D$ is the eigenvector of the water diffusion tensor, and the column vector of the matrix $\overline{C}$ consists of the eigenvalues of the conductivity tensor.

In addition, conductivity exhibits different properties depending on the frequency of applied current. The respective conductivities at low frequencies (<1 kHz) and high frequencies (100 to 200 MHz) are expressed by Equation 3 below:

$$\sigma_H = \alpha c_e m_e + (1-\alpha) c_i m_i$$

$$\sigma_L = \alpha c_e m_e \qquad \text{[Equation 3]}$$

wherein each coefficient is shown in Table 1 below:

TABLE 1

| | |
|---|---|
| Extracellular ion concentration | $c_e$ |
| Intracellular ion concentration | $c_i$ |

TABLE 1-continued

| | |
|---|---|
| Extracellular isotropic ion mobility | $m_e$ |
| Intracellular isotropic ion mobility | $m_i$ |
| Extracellular isotropic water diffusion coefficient | $d_e$ |
| Intracellular isotropic water diffusion coefficient | $d_i$ |
| Extracellular anisotropic ion mobility | $M_e$ |
| Extracellular anisotropic water diffusion tensor | $D_e$ |
| Volume fraction of extracellular space | $\alpha$ |
| High-frequency isotropic conductivity | $\sigma_H$ |
| Low-frequency isotropic conductivity | $\sigma_L$ |
| Low-frequency anisotropic conductivity tensor | $\Lambda_L$ |

As shown above, conductivities at high and low frequencies differ depending on the ion mobility, volume fraction, and ion concentrations of intracellular and extracellular spaces.

As a representative example of the conventional method of obtaining conductivity at a low frequency, there is a magnetic resonance electric impedance tomography (MREIT) method of obtaining the distribution of current density and conductivity by injecting low-frequency current from the outside.

In addition, as a representative example of the conventional method of obtaining a conductivity distribution at high frequency, there is a magnetic resonance electric properties tomography (MR-EPT) method of obtaining conductivity using the phase signal of a high-frequency magnetic field.

According to the MREIT method, the magnetic density $B_z$ in the direction of an internal main magnetic field by current injection is measured using a complex signal obtained by injecting current from the outside and expressed by Equation 4 below, and the measured $B_z$ signal is used to reconstruct current density or conductivity inside the human body or an object. The MREIT method has recently been extensively studied.

$$M^\pm(x,y) = \rho(x,y)\exp(i\phi(x,y) \pm i\gamma B_z(x,y)T_c), \qquad \text{[Equation 4]}$$

wherein $M^\pm$ denotes a complex signal measured by varying the direction of current, $\rho$ denotes an MR magnitude signal, $B_z$ denotes magnetic density in the direction of a main magnetic field by current injection, and $T_c$ denotes current injection time.

However, in a conventional method of reconstructing low-frequency conductivity images, since the MREIT method requiring current injection from the outside is used, a small amount of current injected may result in a low signal-to-noise ratio of the measured magnetic field, and low-frequency current should be injected from the outside.

On the other hand, in the MR-EPT method, Equation 5 below representing a magnetic field component measured by the $B_1$ mapping technique satisfies Equation 6 below:

$$H^+ = \frac{1}{2}(H_x + iH_y) \qquad \text{[Equation 5]}$$

$$-\nabla^2 H^+(r) = \frac{1}{2}((\hat{x} + i\hat{y}) \times \nabla \times H(r)) \cdot \frac{\nabla k(r)}{k(r)} - i\omega\mu_0(r)H^+(r), \qquad \text{[Equation 6]}$$

wherein $\hat{x}$ denotes (1,0,0), $\hat{y}$ denotes (0,1,0), k denotes admittivity, $\omega$ denotes each frequency, and $\mu_0$ denotes magnetic permeability.

In this case, assuming, in part, $$\frac{\nabla k}{k} \approx 0,$$

in the MR-EPT method, Equation 7 below, which is an algebraic equation of the measured phase signal, is used:

$$\sigma_H(r) = \frac{i}{w\mu_0} \frac{\nabla^2 H^+(r)}{H^+(r)}$$ [Equation 7]

In Equation 7, reconstructed high-frequency conductivity has a value that is the sum of the electrical properties of intracellular and extracellular spaces.

Therefore, the present invention is intended to solve the constraint conditions of the MREIT method requiring external current injection. In the present invention, a method of reconstructing low-frequency conductivity images using the MR-EPT method capable of obtaining information on high-frequency conductivity without current injection and the diffusion coefficient imaging method in which a plurality of diffusion weighting factor b values of MRI are applied is disclosed.

RELATED ART DOCUMENTS

Patent Document

U.S. Pat. No. 7,627,155 (Dec. 1, 2009), "FAST GEOMETRIC FLOWS BASED WHITE MATTER FIBER TRACT SEGMENTATION IN DT-MRI"

Non-Patent Documents

IEEE Transactions on Biomedical Engineering. 61(5). 2014, "Electrical tissue property imaging at low frequency using MREIT"

Physiological Measurement 29(2008) R1-R26, "Magnetic resonance electrical impedance tomography (MREIT) for high-resolution conductivity imaging"

Magnetic Resonance in Medicine 37(1997), "An analytical model of restricted diffusion in bovine optic nerve"

NeuroImage 61(2012), "NODDI: Practical in vivo neurite orientation dispersion and density imaging of the human brain"

DISCLOSURE

Technical Problem

Therefore, the present invention has been made in view of the above problems, and it is one object of the present invention to provide a device and method for reconstructing low-frequency conductivity images using MRI without current injection. According to the present invention, low-frequency conductivity images in a subject to be measured such as the human body and an object may be reconstructed using an MRI device without applying current to the subject, and conductivity tractography images may be implemented using reconstructed low-frequency conductivity tensor images.

It is another object of the present invention to provide a device and method for reconstructing low-frequency conductivity images using MRI without current injection. According to the present invention, low-frequency conductivity images may be reconstructed using a diffusion coefficient imaging method for extracting information about the volume fraction of the extracellular space ($\alpha$) and the diffusion coefficients of each space ($d_e$, $d_i$) using the difference between an MR signal obtained by applying a plurality of diffusion weighting factor b values and an MR signal obtained without diffusion weighting factor b values.

It is another object of the present invention to provide a device and method for reconstructing low-frequency conductivity images using MRI without current injection. According to the present invention, the diffusion coefficients and volume fractions of the intracellular and extracellular spaces may be extracted using an MR-EPT method capable of obtaining information on high-frequency conductivity without current injection from the outside and using the water diffusion tensor measured by applying a plurality of diffusion weighting factor b values and water diffusion gradients to calculate low-frequency conductivity.

It is yet another object of the present invention to provide a device and method for reconstructing low-frequency conductivity images using MRI without current injection. According to the present invention, information on ion concentration in a subject may be obtained using MR-EPT, the directional tensor of ions may be calculated from the water diffusion tensor, and low-frequency conductivity may be calculated by multiplying the calculated directional tensor by the obtained ion concentration.

Technical Solution

In accordance with one aspect of the present invention, provided is a device for reconstructing low-frequency conductivity images using MRI according to an embodiment of the present invention, including an acquisition part for obtaining a relationship between ion concentration ($C_s$) and mobility within intracellular/extracellular spaces of a subject to be measured by reconstructing high-frequency conductivity from magnetic resonance electric properties tomography (MR-EPT), and obtaining an MR signal using multi-b-value diffusion-weighted imaging; a calculation part for calculating a directional tensor of ions ($M_L$) using a water diffusion tensor (D) calculated from a volume fraction of an extracellular space ($\alpha$) and diffusion weighting factors (b), and calculating a low-frequency conductivity tensor from the calculated directional tensor of ions and the obtained high-frequency conductivity; and an image reconstruction part for reconstructing low-frequency conductivity images based on low-frequency conductivity from the calculated low-frequency conductivity tensor.

In the calculation part, the volume fraction of the extracellular space may be calculated by applying the diffusion weighting factors and water diffusion gradients for distinguishing cellular spaces in a subject, and the water diffusion tensor is calculated by extracting diffusion coefficients in the intracellular/extracellular spaces from the calculated volume fraction of the extracellular space and the diffusion weighting factors.

In the calculation part, the volume fractions of the intracellular/extracellular spaces may be extracted by applying a plurality of diffusion gradients, or the volume fractions of the intracellular/extracellular spaces may be measured using MR signal attenuation using a multi-echo spin echo measurement method.

In the calculation part, the water diffusion gradients may be calculated using volume fractions of intracellular/extracellular spaces extracted by applying a plurality of diffusion gradients, diffusion coefficients extracted from the diffusion gradients, and the high-frequency conductivity.

In the calculation part, the low-frequency conductivity may be calculated from at least one of the calculated directional tensor of ions, the volume fraction of the extracellular space, the high-frequency conductivity, and the diffusion coefficients.

In the calculation part, the low-frequency conductivity may be calculated from at least one of the calculated directional tensor of ions, the volume fraction of the extracellular space, the high-frequency conductivity, and the diffusion coefficients.

In the acquisition part, the high-frequency conductivity combined with conductivities of the intracellular and extracellular spaces of the subject may be reconstructed using a phase signal from a high frequency magnetic field using MR-EPT without external current injection.

In the acquisition part, the volume fractions and diffusion coefficients in the intracellular/extracellular spaces may be obtained by reconstructing a coefficient of an exponential function of the MR signal depending on the magnetic field strength using the multi-b-value diffusion-weighted imaging by applying a plurality of diffusion gradients.

In the acquisition part, information on the ion concentration may be obtained using diffusion tensor MRI (DT-MRI) for measuring three-dimensional diffusion characteristics of water molecules in tissue of the subject, and information on the high-frequency conductivity combined with the concentrations and mobility of ions in the intracellular/extracellular spaces is obtained from the reconstructed high-frequency conductivity.

In the image reconstruction part, the low-frequency conductivity images may be reconstructed using the volume fractions of the intracellular/extracellular spaces and a diffusion coefficient imaging method for extracting diffusion coefficients of each region.

In accordance with another aspect of the present invention, provided is a method of reconstructing low-frequency conductivity images using MRI according to an embodiment of the present invention, including a step of obtaining the relationship between concentration ($C_s$) and mobility of ions in all intracellular/extracellular spaces in a subject to be measured by reconstructing high-frequency conductivity in the subject from magnetic resonance electric properties tomography (MR-EPT), and obtaining an MR signal using multi-b-value diffusion-weighted imaging; a step of calculating the directional tensor of ions ($M_L$) using the water diffusion tensor (D) calculated from the volume fraction of the extracellular space ($\alpha$) and diffusion weighting factors (b); a step of calculating a low-frequency conductivity tensor from the information about the calculated directional tensor of ions and the obtained ion concentration; and a step of reconstructing low-frequency conductivity images based on low-frequency conductivity from the calculated low-frequency conductivity tensor.

Advantageous Effects

According to an embodiment of the present invention, low-frequency conductivity images in a subject to be measured such as the human body and an object can be reconstructed using an MRI device without applying current to the subject, and conductivity tractography images can be implemented using reconstructed low-frequency conductivity tensor images.

In addition, according to an embodiment of the present invention, low-frequency conductivity images can be reconstructed using a diffusion coefficient imaging method for extracting information about the volume fractions of intracellular and extracellular spaces ($\alpha$) and the diffusion coefficients of each space ($d_e$, $d_i$) using the difference between an MR signal obtained by applying a plurality of diffusion weighting factor b values and an MR signal obtained without diffusion weighting factor b values.

In addition, according to an embodiment of the present invention, the diffusion coefficients and volume fractions of the intracellular and extracellular spaces can be extracted using an MR-EPT method capable of obtaining information on high-frequency conductivity without current injection from the outside and using the water diffusion tensor measured by applying a plurality of diffusion weighting factor b values and water diffusion gradients to calculate low-frequency conductivity.

In addition, according to an embodiment of the present invention, information on ion concentration in a subject can be obtained using MR-EPT, the directional tensor of ions can be calculated from the water diffusion tensor, and low-frequency conductivity can be calculated by multiplying the calculated directional tensor by the obtained ion concentration.

DESCRIPTION OF DRAWINGS

FIG. 3 is a flowchart for explaining a method of reconstructing low-frequency conductivity images using MRI according to an embodiment of the present invention.

BEST MODE

Figure 1:
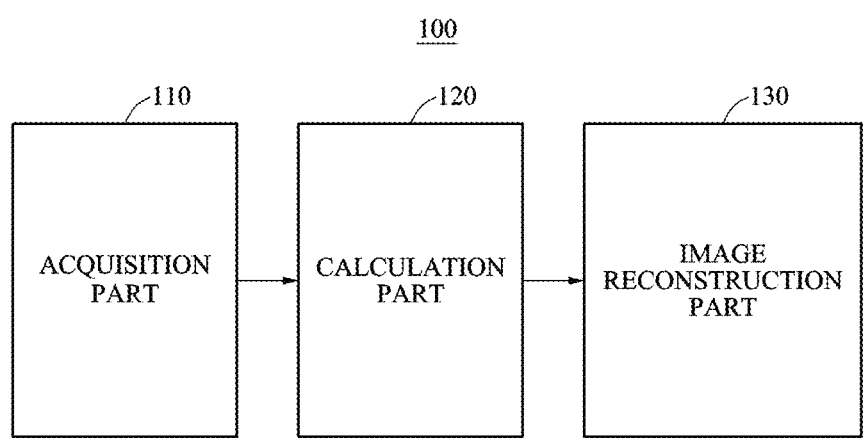
FIG. 1 is a block diagram for explaining the configuration of a device for reconstructing low-frequency conductivity images using MRI according to an embodiment of the present invention.

The present invention will now be described more fully with reference to the accompanying drawings and contents disclosed in the drawings. However, the present invention should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context. It will be further understood that the terms "comprise" and/or "comprising", when used in this specification, specify the presence of stated components, steps, operations, and/or elements, but do not preclude the presence or addition of one or more other components, steps, operations, and/or elements thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the disclosure and the appended claims, the singular forms "a", "an" and "the" are intended to include the plural forms as well, unless context clearly indicates otherwise.

In addition, terms such as "first" and "second" are used herein merely to describe a variety of constituent elements, but the constituent elements are not limited by the terms. The terms are used only for the purpose of distinguishing one constituent element from another constituent element.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

Meanwhile, in the following description of the present invention, a detailed description of known functions and configurations incorporated herein will be omitted when it may make the subject matter of the present invention unclear. The terms used in the specification are defined in consideration of functions used in the present invention, and can be changed according to the intent or conventionally used methods of clients, operators, and users. Accordingly, definitions of the terms should be understood on the basis of the entire description of the present specification.

FIG. 1 is a block diagram for explaining the configuration of a device for reconstructing low-frequency conductivity images using MRI according to an embodiment of the present invention.

Referring to FIG. 1, in the device for reconstructing low-frequency conductivity images using MRI 100 according to an embodiment of the present invention, high-frequency conductivity in a subject obtained using MR-EPT is reconstructed to obtain the relationship between ion concentration and mobility in the intracellular/extracellular spaces of the subject and to obtain an MR signal, the directional tensor of ions is calculated from the water diffusion tensor, and low-frequency conductivity is calculated from the calculated directional tensor of ions and the obtained high-frequency conductivity to reconstruct low-frequency conductivity images.

More specifically, the device for reconstructing low-frequency conductivity images using MRI 100 according to an embodiment of the present invention obtains high-frequency conductivity from a phase signal in a subject using MR-EPT, and obtains an MR signal from multi-b-value diffusion-weighted imaging by applying a plurality of diffusion gradients.

In addition, the device for reconstructing low-frequency conductivity images using MRI 100 according to an embodiment of the present invention is capable of calculating the volume fraction of the extracellular space and the diffusion coefficients of each space, calculating a low-frequency conductivity tensor from the calculated directional tensor of ions, high-frequency conductivity, the volume fraction of the extracellular space, and diffusion coefficients, and reconstructing low-frequency conductivity images based on low-frequency conductivity according to the calculated low-frequency conductivity tensor.

In addition, the device for reconstructing low-frequency conductivity images using MRI 100 according to an embodiment of the present invention includes an acquisition part 110, a calculation part 120, and an image reconstruction part 130.

In the acquisition part 110, high-frequency conductivity in a subject to be measured is reconstructed from magnetic resonance electric properties tomography (MR-EPT) to obtain the relationship between ion concentration ($C_s$) and mobility, in which the effect in the intracellular/extracellular spaces of the subject is combined, and an MR signal is obtained from multi-b-value diffusion-weighted imaging by applying a plurality of water diffusion gradients.

According to an embodiment, in the acquisition part 110, MR phase signal analysis may be used. In addition, from multi-b-value diffusion-weighted imaging for distinguishing the ion mobility and the intracellular and extracellular spaces, all data according to the intensity and direction of a diffusion magnetic field may be obtained through comparison of signals according to whether or not the diffusion magnetic field is applied.

In this case, since the degree of water is influenced by at least one of ion concentrations in intracellular and extracellular spaces, viscosity, and cell size and shape, the volume fraction and diffusion coefficient corresponding to the extracellular space of tissue in an MR image may be obtained using a plurality of diffusion weighting factors (multi-b).

In addition, in the acquisition part 110, high-frequency conductivity combined with the conductivities of the intracellular and extracellular spaces of a subject may be reconstructed from the phase signal of a high frequency magnetic field using MR-EPT without current injection from the outside.

For example, in the acquisition part 110, MR-EPT is used to reconstruct high-frequency conductivity without current injection from the outside. In this case, MR-EPT may be a method of reconstructing the electrical permittivity and conductivity distribution of an electrically conductive object as images, and may provide permittivity (complex permittivity) images in a range of 100 to 200 MHz using the standard RF coil of the MR system.

According to an embodiment, in the acquisition part 110, high-frequency conductivity combined with the conductivities of the intracellular and extracellular spaces of a subject to be measured, relates to the relationship between the ion concentrations ($c_e$, $c_i$) and mobility ($m_e$, $m_i$) of the intracellular and extracellular spaces, as shown in Equation 8 below:

$$\sigma_H = \alpha c_e m_e + (1-\alpha) c_i m_i \quad \text{[Equation 8]}$$

wherein each coefficient is shown in Table 1 described above.

In addition, based on Equation 8, the relationship between the concentration ($c_i$) of ions with electrical properties in the intracellular space and the concentration ($c_e$) of ions with electrical properties in the extracellular space may be defined by relation of $c_i = \beta c_e$. In this case, the coefficient $\beta$ may be extracted, but may be used as a known reference value.

In addition, when the relation ($c_i = \beta c_e$) is used, the relationship between extracellular ion concentration ($c_e$) and high-frequency conductivity ($\sigma_H$) from Equation 8 may be expressed by Equation 9 below:

$$c_e = \frac{\sigma_H}{\alpha m_e + (1-\alpha) \beta m_i}, \quad \text{[Equation 9]}$$

wherein the mobility ($m_i$, $m_e$) of the intracellular and extracellular spaces may satisfy Equation 10 below, which is the Einstein relation, for defining the relationship between ion mobility and diffusion coefficient:

$$m_e = \frac{q}{kT} d_e, \quad m_i = \frac{q}{kT} d_i, \quad \text{[Equation 10]}$$

wherein q denotes quantity of electric charge, k denotes the Boltzmann constant, and T denotes temperature.

In addition, diffusion coefficients $d_e$ and $d_i$ that affect high-frequency conductivity may be assumed to be diffusion coefficients in a homogeneous state without being affected by the cell membrane.

Referring again to FIG. 1, in the acquisition part 110 of the device for reconstructing low-frequency conductivity images using MRI 100 according to an embodiment of the present invention, MR signals including the volume fractions and diffusion coefficients of the intracellular and extracellular spaces may be obtained by applying a diffusion magnetic field according to the intensity of a magnetic field using multi-b-value diffusion-weighted imaging.

In addition, in the acquisition part 110, information about combined conductivities in the intracellular and extracellular spaces may be obtained from the reconstructed high-frequency conductivity, and ion mobility may be obtained using diffusion tensor MRI (DT-MRI) for measuring the three-dimensional diffusion characteristics of water molecules in the tissue of a subject.

In the acquisition part 110, the properties (volume fractions and diffusion coefficients) of the intracellular and extracellular spaces according to the three-dimensional diffusion characteristics of water molecules in the tissue of a subject may be obtained using a plurality of diffusion weighting factors (multi-b).

In the calculation part 120, the directional tensor of ions ($M_L$) is calculated using the water diffusion tensor (D) calculated from the volume fraction of the extracellular space (α) and diffusion weighting factors (b), and low-frequency conductivity ($\Sigma_e$) is calculated from the calculated directional tensor of ions and the obtained high-frequency conductivity.

More specifically, in the calculation part 120, the directional tensor of ions ($M_L$) may be calculated from the water diffusion tensor (D) measured by applying water diffusion gradients, and low-frequency conductivity may be calculated using the calculated directional tensor of ions and the obtained high-frequency conductivity.

In addition, in the calculation part 120, the value of the extracellular ion concentration ($c_e$) calculated in Equation 9 is input to Equation 3 of the low-frequency conductivity, and the low-frequency conductivity tensor in the extracellular space may be calculated from Equation 11 below:

$$\Sigma_e = \frac{\alpha \sigma_H}{\alpha m_e + (1-\alpha)\beta m_i} M_e,$$  [Equation 11]

wherein each coefficient is shown in Table 1 described above.

The low-frequency conductivity tensor ($\Sigma_e$) expressed by a mobility equation may be expressed by Equation 12 below, a diffusion coefficient equation, by the Einstein relation that defines the relationship between ion mobility and diffusion coefficient:

$$\Sigma_e = \frac{\alpha \sigma_H}{\alpha d_e + (1-\alpha)\beta d_i} D_e,$$  [Equation 12]

wherein each coefficient is shown in Table 1 described above.

In addition, in the calculation part 120, the volume fraction of the extracellular space (α) may be calculated by applying diffusion weighting factors (b) for distinguishing cell spaces in a subject and water diffusion gradients, and the diffusion coefficients of the intracellular/extracellular spaces may be extracted from the calculated volume fraction of the extracellular space and diffusion weighting factors, and the water diffusion tensor may be calculated.

In addition, in the calculation part 120, the relationship between high-frequency conductivity, the volume fraction of the extracellular space, and the diffusion coefficients of the intracellular/extracellular spaces may be calculated.

In addition, in the calculation part 120, a low-frequency conductivity tensor may be calculated from the calculated directional tensor of ions, the volume fraction of the extracellular space, the high-frequency conductivity, and the diffusion coefficients.

For example, in the calculation part 120, low-frequency conductivity may be calculated using at least one of the calculated directional tensor of ions, the volume fraction of the extracellular space, the high-frequency conductivity, and the diffusion coefficients.

As described above, the components of a low-frequency conductivity tensor may be determined from at least one of the high-frequency conductivity, the diffusion coefficients, and the volume fraction of the extracellular space.

Referring again to FIG. 1, in the image reconstruction part 130 of the device for reconstructing low-frequency conductivity images using MRI 100 according to an embodiment of the present invention, low-frequency conductivity images are reconstructed based on calculated low-frequency conductivity.

In the image reconstruction part 130, low-frequency conductivity images may be reconstructed using the diffusion coefficient imaging method in which information about the volume fractions of the intracellular/extracellular spaces and the diffusion coefficients of each space is extracted.

More specifically, in the image reconstruction part 130, low-frequency conductivity images may be reconstructed using a diffusion coefficient imaging method of extracting information about the volume fractions of the intracellular and extracellular spaces (α) and the diffusion coefficients of each space ($d_e$, $d_i$) using the difference between an MR signal obtained by applying a plurality of diffusion weighting factor b values and an MR signal obtained without diffusion weighting factor b values.

Figure 2A:
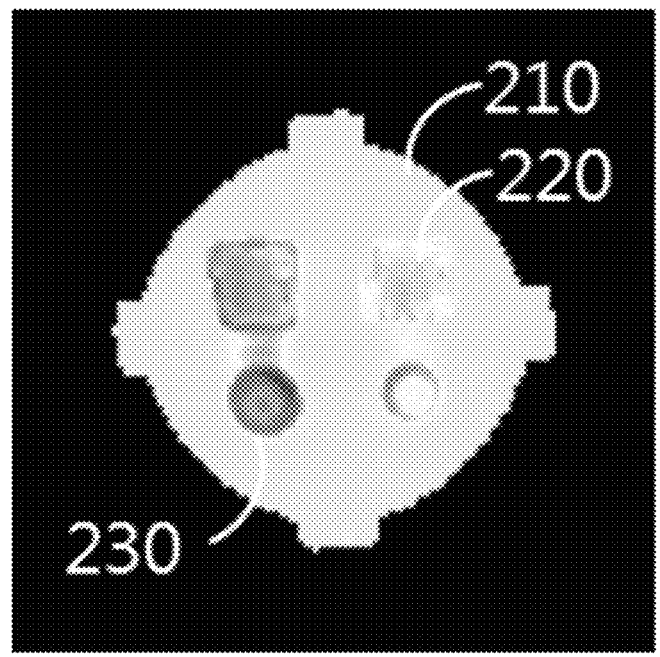
FIGS. 2A to 2C show images reconstructed using a device for reconstructing low-frequency conductivity images using MRI according to an embodiment of the present invention.
Figure 2B:
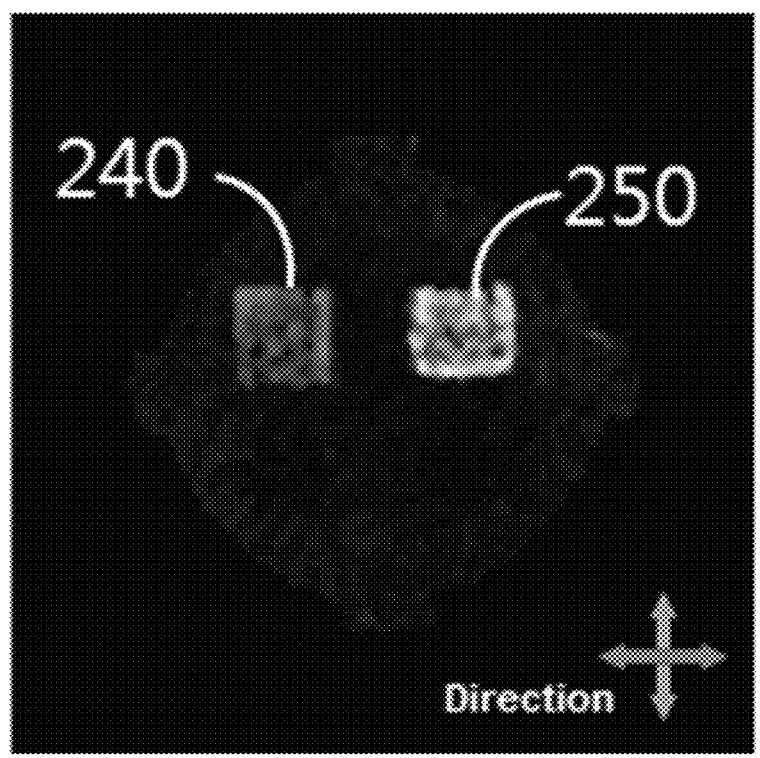
Figure 2C:
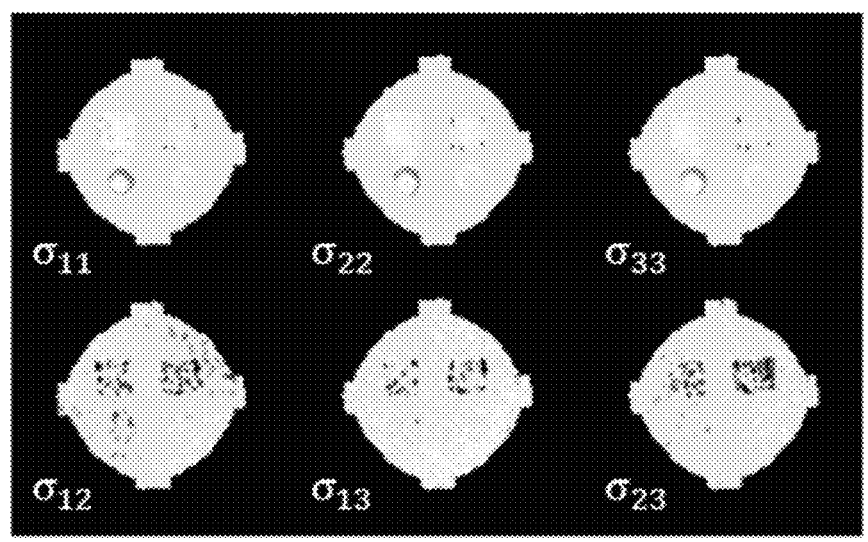

FIGS. 2A to 2C show images reconstructed using a device for reconstructing low-frequency conductivity images using MRI according to an embodiment of the present invention.

More specifically, FIG. 2A shows high-frequency conductivity images in a subject obtained using MR-EPT according to an embodiment of the present invention, and FIG. 2B shows images of the directional tensor of ions obtained using the water diffusion tensor.

In addition, FIG. 2C shows images of low-frequency conductivity obtained from ion concentrations in a subject and the directional tensor of ions.

More specifically, FIG. 2A shows background conductivity 210 obtained from MR-EPT, high-frequency conductivity 220 in a subject, and high-frequency conductivity 230 in agar with a controlled conductivity value.

In this case, the subject may be muscle tissue, but the type of the subject is not limited thereto.

FIG. 2B shows calculated water diffusion directionality after applying diffusion gradients, and shows diffusion direction coefficients calculated by an image 240 of a subject aligned in the x-axis direction and an image 250 of the subject aligned in the y-axis direction.

In addition, FIG. 2C shows images of the low-frequency conductivity according to the matrix directions of $\sigma_{11}$, $\sigma_{12}$, $\sigma_{13}$, $\sigma_{22}$, $\sigma_{23}$ and $\sigma_{33}$ using a device for reconstructing low-frequency conductivity images using MRI according to an embodiment of the present invention.

FIG. 3 is a flowchart for explaining a method of reconstructing low-frequency conductivity images using MRI according to an embodiment of the present invention.

Referring to FIG. 3, according to a method of reconstructing low-frequency conductivity images using MRI according to an embodiment of the present invention, in step 310, high-frequency conductivity in a subject to be measured is reconstructed from magnetic resonance electric properties tomography (MR-EPT) to obtain the relationship between ion concentration ($C_S$) and mobility in the intracellular/extracellular spaces of the subject, and an MR signal is obtained using multi-b-value diffusion-weighted imaging.

In step 310, high-frequency conductivity combined with the conductivities of the intracellular and extracellular spaces of a subject, may be reconstructed from the phase signal of a high frequency magnetic field using MR-EPT without current injection from the outside.

For example, in step 310, MR-EPT may be used to reconstruct high-frequency conductivity without current injection from the outside, and MR-EPT may be a method of reconstructing the electrical permittivity and conductivity distribution of an electrically conductive object as images, and MR-EPT may provide permittivity (complex permittivity) images in a range of 100 to 200 MHz using the standard RF coil of the MR system.

In addition, in step 310, information about the combined conductivities in the intracellular and extracellular spaces may be obtained from reconstructed high-frequency conductivity, and ion mobility may be obtained using diffusion tensor MRI (DT-MRI) for measuring the three-dimensional diffusion characteristics of water molecules in the tissue of a subject.

In step 320, the directional tensor of ions ($M_L$) is calculated using the water diffusion tensor (D) calculated from the volume fraction of the extracellular space (a) and diffusion weighting factors (b).

In step 320, the directional tensor of ions ($M_L$) may be calculated from the water diffusion tensor (D) measured by applying water diffusion gradients.

In step 330, a low-frequency conductivity tensor is calculated from the calculated directional tensor of ions and the obtained ion concentration.

For example, in step 330, low frequency conductivity may be calculated from at least one of the calculated directional tensor of ions, the volume fraction of the extracellular space, high-frequency conductivity, and diffusion coefficients.

In step 340, based on low-frequency conductivity according to the calculated low-frequency conductivity tensor, low-frequency conductivity image is reconstructed.

In step 340, the low-frequency conductivity image may be reconstructed using the diffusion coefficient imaging method in which information about the volume fractions of the intracellular/extracellular spaces and the diffusion coefficients of each space is extracted.

Although the present invention has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

DESCRIPTION OF SYMBOLS

100: DEVICE FOR RECONSTRUCTING LOW-FREQUENCY CONDUCTIVITY IMAGES USING MRI
110: ACQUISITION PART
120: CALCULATION PART
130: IMAGE RECONSTRUCTION PART

The invention claimed is:

1. A device for reconstructing low-frequency conductivity images using MRI without current injection, comprising:
   a memory configured to store computer-readable instructions; and
   one or more processors configured to execute the computer-readable instructions such that the one or more processors are configured to:
   obtain a relationship between concentration (Cs) and mobility of ions within intracellular/extracellular spaces of a subject to be measured by reconstructing high-frequency conductivity from magnetic resonance electric properties tomography (MR-EPT), and obtain an MR signal using multi-b-value diffusion-weighted imaging;
   calculate a directional tensor of ions ($M_L$) using a water diffusion tensor (D) calculated from a volume fraction of an extracellular space ($\alpha$) and diffusion weighting factors (b), and calculate a low-frequency conductivity tensor from the calculated directional tensor of ions and the obtained high-frequency conductivity; and
   reconstruct low-frequency conductivity images based on low-frequency conductivity from the calculated low-frequency conductivity tensor,
   wherein that the one or more processors are configured to:
   obtain the relationship between the icon concentrations ($c_e$, $c_i$) and mobility ($m_e$, $m_i$) of the intracellular and extracellular spaces, as shown in Equation 1 below:

$$\sigma_H = \alpha c_e m_e + (1-\alpha) c_i m_i, \qquad \text{[Equation 1]}$$

wherein when the relation ($c_i = \beta c_e$) is used, the relationship between extracellular ion concentration ($c_e$) and high-frequency conductivity ($\sigma_H$) from Equation 1 is expressed by Equation 2 below:

$$c_e = \frac{\sigma_H}{\alpha m_e + (1-\alpha)\beta m_i}, \qquad \text{[Equation 2]}$$

wherein the mobility ($m_i$, $m_e$) of the intracellular and extracellular spaces satisfy Equation 3 below, which is the Einstein relation, for defining the relationship between ion mobility and diffusion coefficient:

$$m_e = \frac{q}{kT} d_e,$$
   $$m_i = \frac{q}{kT} d_i, \qquad \text{[Equation 3]}$$

wherein q denotes quantity of electric charge, k denotes the Boltzmann constant, and T denotes temperature, and wherein diffusion coefficients $d_e$ and $d_i$ that affect high-frequency conductivity are assumed to be diffusion coefficients in a homogeneous state without being affected by the cell membrane.

2. The device according to claim 1, wherein the one or more processors are configured to calculate the volume fraction of the extracellular space by applying the diffusion weighting factors and water diffusion gradients for distinguishing cellular spaces in a subject, and calculate the water diffusion tensor by extracting diffusion coefficients in the intracellular/extracellular spaces from the calculated volume fraction of the extracellular space and the diffusion weighting factors.

3. The device according to claim 2, wherein the one or more processors are configured to calculate the water diffusion gradients using volume fractions of intracellular/extracellular spaces extracted by applying a plurality of diffusion gradients, diffusion coefficients extracted from the diffusion gradients, and the high-frequency conductivity.

4. The device according to claim 2, wherein the one or more processors are configured to calculate the low-frequency conductivity from at least one of the calculated directional tensor of ions, the volume fraction of the extracellular space, the high-frequency conductivity, and the diffusion coefficients.

5. The device according to claim 1, wherein the one or more processors are configured to reconstruct the high-frequency conductivity combined with conductivities of the intracellular and extracellular spaces of the subject using a phase signal from a high frequency magnetic field using MR-EPT without external current injection.

6. The device according to claim 5, wherein the one or more processors are configured to obtain the volume fractions and diffusion coefficients in the intracellular/extracellular spaces by reconstructing a coefficient of an exponential function of the MR signal depending on the magnetic field strength using the multi-b-value diffusion-weighted imaging by applying a plurality of diffusion gradients.

7. The device according to claim 6, wherein the one or more processors are configured to obtain the ion concentration using diffusion tensor MRI (DT-MRI) for measuring three-dimensional diffusion characteristics of water molecules in tissue of the subject, and obtain information on the high-frequency conductivity combined with the concentrations and mobility of ions in the intracellular/extracellular spaces from the reconstructed high-frequency conductivity.

8. The device according to claim 1, wherein, the one or more processors are configured to reconstruct the low-frequency conductivity images using the volume fractions of the intracellular/extracellular spaces and a diffusion coefficient imaging method for extracting diffusion coefficients of each region.

9. A method of reconstructing low-frequency conductivity images using MRI without current injection, comprising:
a step of obtaining a relationship between the concentration (Cs) and mobility of ions within the intracellular/extracellular spaces of a subject to be measured by reconstructing high-frequency conductivity from magnetic resonance electric properties tomography (MR-EPT), and obtaining an MR signal using multi-b-value diffusion-weighted imaging;
a step of calculating a directional tensor of ions (ML) using a water diffusion tensor (D) calculated from a volume fraction of an extracellular space ( ) and diffusion weighting factors (b);
a step of calculating a low-frequency conductivity tensor from the calculated directional tensor of ions and the obtained ion concentration; and
a step of reconstructing low-frequency conductivity images based on low-frequency conductivity from the calculated low-frequency conductivity tensor,
wherein the step of obtaining comprising:
obtaining the relationship between the ion concentrations ($c_e$, $c_i$) and mobility ($m_e$, $m_i$) of the intracellular and extracellular spaces, as shown in Equation 1 below:

$$\sigma_H = \alpha c_e m_e + (1-\alpha) c_i m_i, \quad \text{[Equation 1]}$$

wherein when the relation ($c_i = \beta c_e$) is used, the relationship between extracellular ion concentration ($c_e$) and high-frequency conductivity ($\sigma_H$) from Equation 1 is expressed by Equation 2 below:

$$c_e = \frac{\sigma_H}{\alpha m_e + (1-\alpha)\beta m_i}, \quad \text{[Equation 2]}$$

wherein the mobility ($m_i$, $m_e$) of the intracellular and extracellular spaces satisfy Equation 3 below, which is the Einstein relation, for defining the relationship between ion mobility and diffusion coefficient:

$$m_e = \frac{q}{kT} d_e,$$
$$m_i = \frac{q}{kT} d_i, \quad \text{[Equation 3]}$$

wherein q denotes quantity of electric charge, k denotes the Boltzmann constant, and T denotes temperature, and
wherein diffusion coefficients $d_e$ and $d_i$ that affect high-frequency conductivity are assumed to be diffusion coefficients in a homogeneous state without being affected by the cell membrane.

* * * * *